(12) United States Patent
Quintini et al.

(10) Patent No.: US 12,257,109 B2
(45) Date of Patent: Mar. 25, 2025

(54) SURGICAL-IMPLEMENT COUNT AND CAPTURE SYSTEM

(71) Applicant: The Cleveland Clinic Foundation, Cleveland, OH (US)

(72) Inventors: Cristiano Quintini, Beachwood, OH (US); William Kolosi, Stow, OH (US); Thomas Kadavy, Bellevue, WA (US); Jose Romero, Avon, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 836 days.

(21) Appl. No.: 17/462,204

(22) Filed: Aug. 31, 2021

(65) Prior Publication Data

US 2022/0061953 A1    Mar. 3, 2022

Related U.S. Application Data

(60) Provisional application No. 63/073,182, filed on Sep. 1, 2020.

(51) Int. Cl.
*A61B 90/00* (2016.01)
*A61B 17/06* (2006.01)
(Continued)

(52) U.S. Cl.
CPC ........ *A61B 90/08* (2016.02); *A61B 17/06114* (2013.01); *A61B 50/20* (2016.02);
(Continued)

(58) Field of Classification Search
CPC ... A61B 90/08; A61B 17/06114; A61B 50/20; A61B 2050/002; A61B 2050/21;
(Continued)

(56) References Cited

U.S. PATENT DOCUMENTS 5,667,073 A * 9/1997 Okui .................. H05K 13/0084
206/713
6,476,376 B1 * 11/2002 Biegelsen .......... H04N 1/00681
250/221

(Continued)

FOREIGN PATENT DOCUMENTS

CN    110668140 A    1/2020
KR    102134881 B1    7/2020
(Continued)

OTHER PUBLICATIONS

International Search Report & Written Opinion issued in corresponding application No. PCT/US2021/048396 dated Apr. 4, 2022, 21 pages.

*Primary Examiner* — A. Hunter Wilder
(74) *Attorney, Agent, or Firm* — Tucker Ellis LLP

(57) ABSTRACT

A surgical-implement count and capture system including a carrier tape having a plurality of spaced-apart receiving areas disposed longitudinally along the carrier tape. Each of the plurality of spaced-apart receiving areas being configured to receive a surgical-implement. The carrier tape is configured to follow a first pathway. A deposit station is located along the first pathway and is adapted to accommodate deposition of a plurality of the surgical-implements respectively into successive ones of the spaced-apart receiving areas when resident at the deposit station. A counting station is located along the first pathway downstream of the deposit station. The counting station includes a sensor adapted to detect the plurality of the surgical-implements in the respective receiving areas.

23 Claims, 10 Drawing Sheets

(51) Int. Cl.
*A61B 50/00* (2016.01)
*A61B 50/20* (2016.01)

(52) U.S. Cl.
CPC ..... *A61B 2050/002* (2016.02); *A61B 2050/21* (2016.02); *A61B 2090/0805* (2016.02)

(58) Field of Classification Search
CPC ...... A61B 2090/0805; A61B 17/06161; A61B 50/36; A61B 50/362; A61B 2090/0804; B65B 57/10; B65B 57/20; B65B 15/04; B65B 65/08; B65B 9/045
See application file for complete search history.

(56) References Cited

U.S. PATENT DOCUMENTS

2005/0033259 A1 2/2005 Stravitz
2005/0245845 A1* 11/2005 Roe .................. A61B 5/15153 600/583
2005/0274454 A1* 12/2005 Extrand .................. C09J 11/04 428/323
2007/0074996 A1* 4/2007 Nice .................. H05K 13/0084 206/714
2011/0108190 A1* 5/2011 Dagenbach ......... B32B 38/0008 156/510
2012/0090282 A1 4/2012 Tsumura
2015/0151908 A1 6/2015 Schofield et al.
2019/0224404 A1* 7/2019 Fox .................... A61M 5/3205
2019/0362839 A1 11/2019 Quintini et al.

FOREIGN PATENT DOCUMENTS

WO 2004047660 A1 6/2004
WO 2013008844 A1 1/2013
WO WO-2018132527 A1 * 7/2018 .......... G06F 16/538
WO 2019090132 A1 5/2019

* cited by examiner

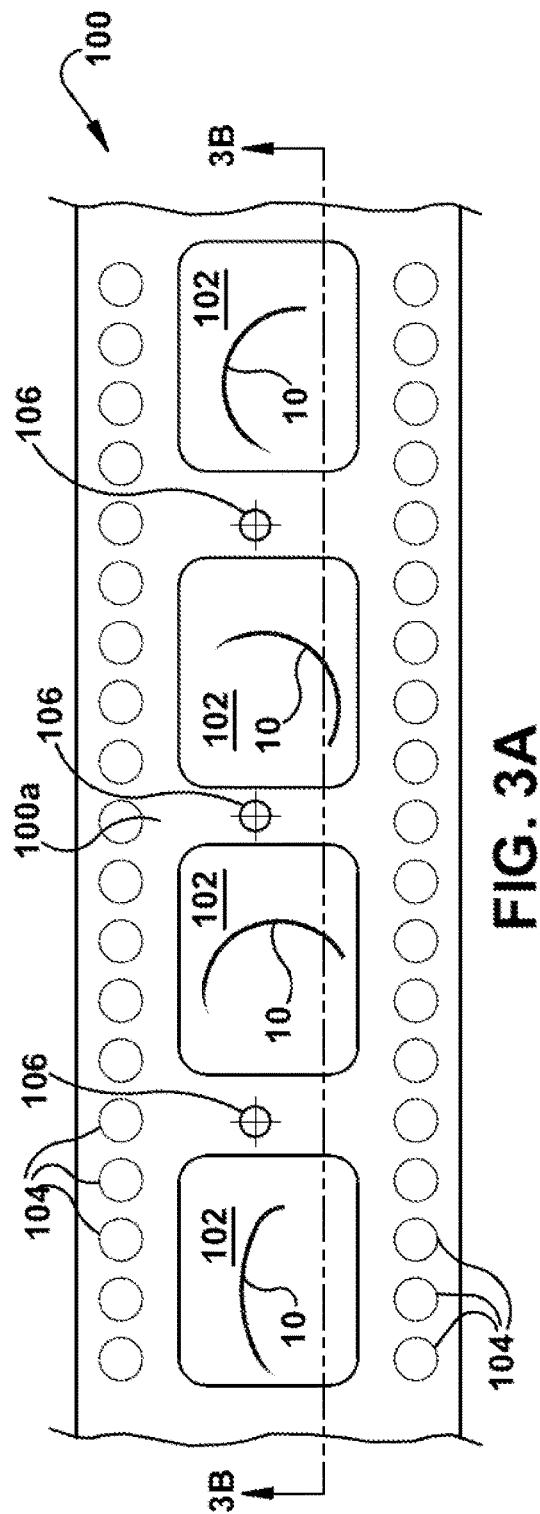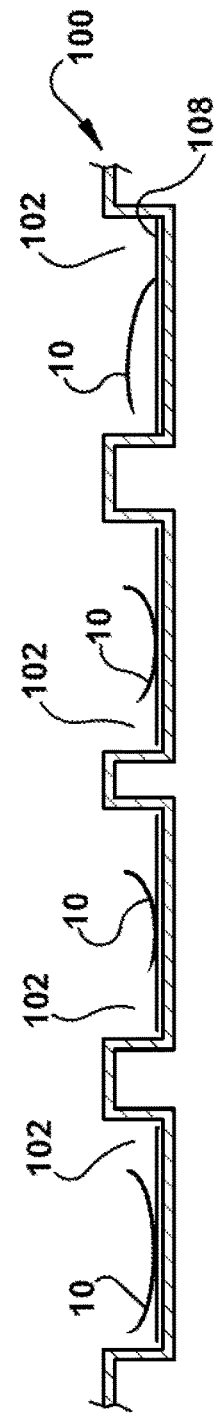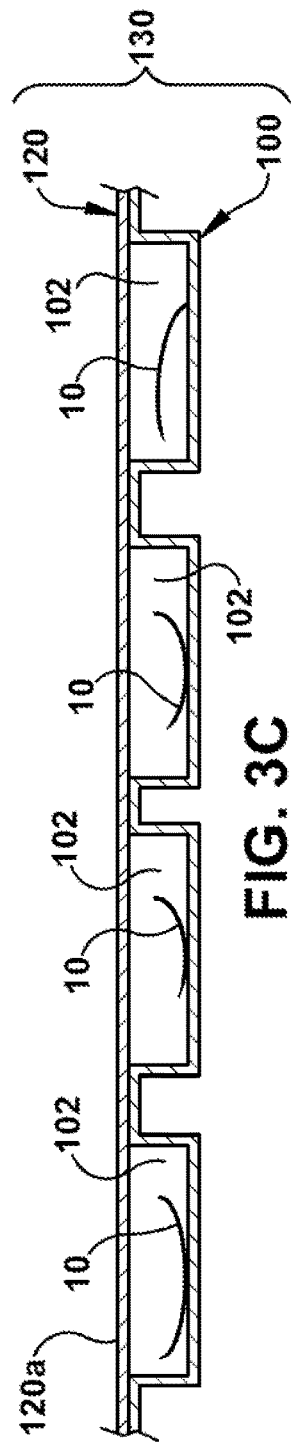

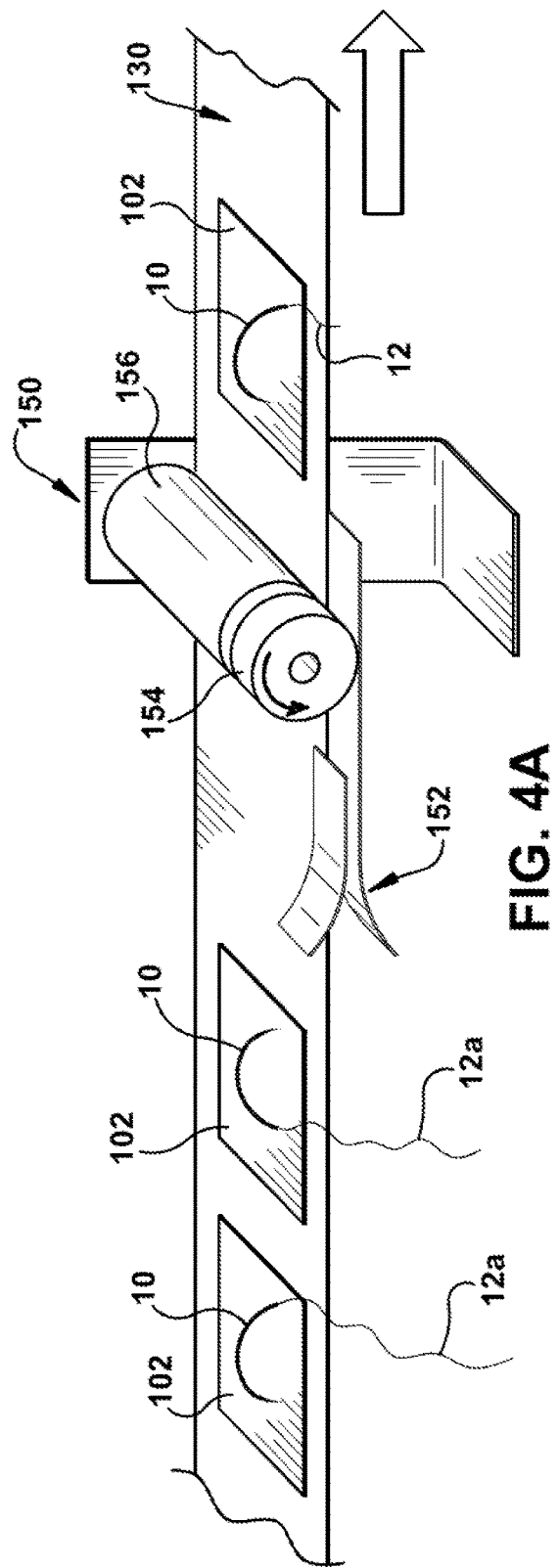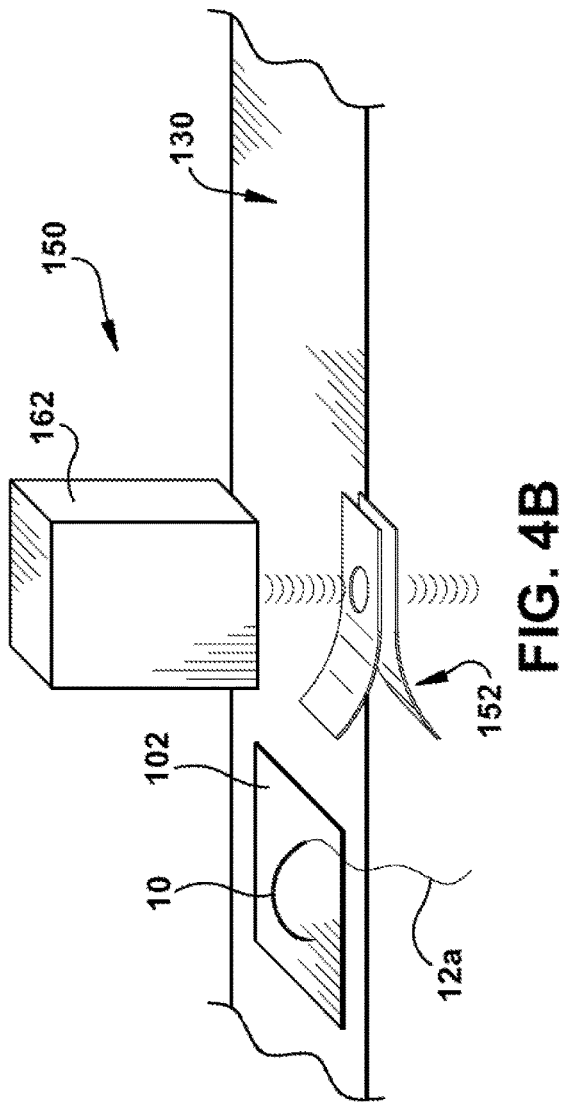

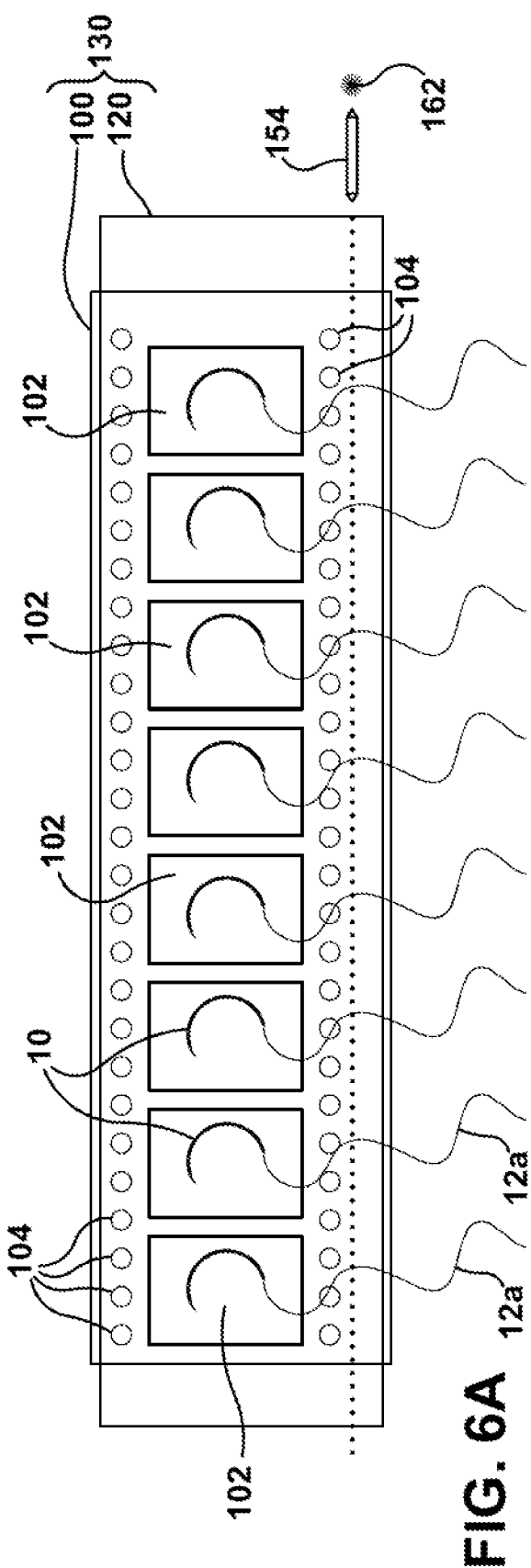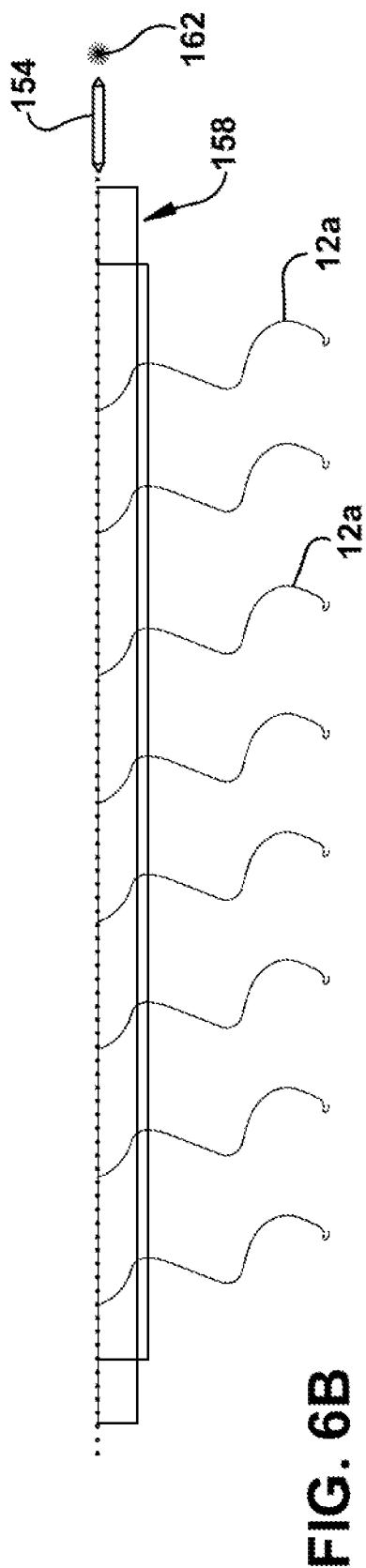
FIG. 6A
FIG. 6B

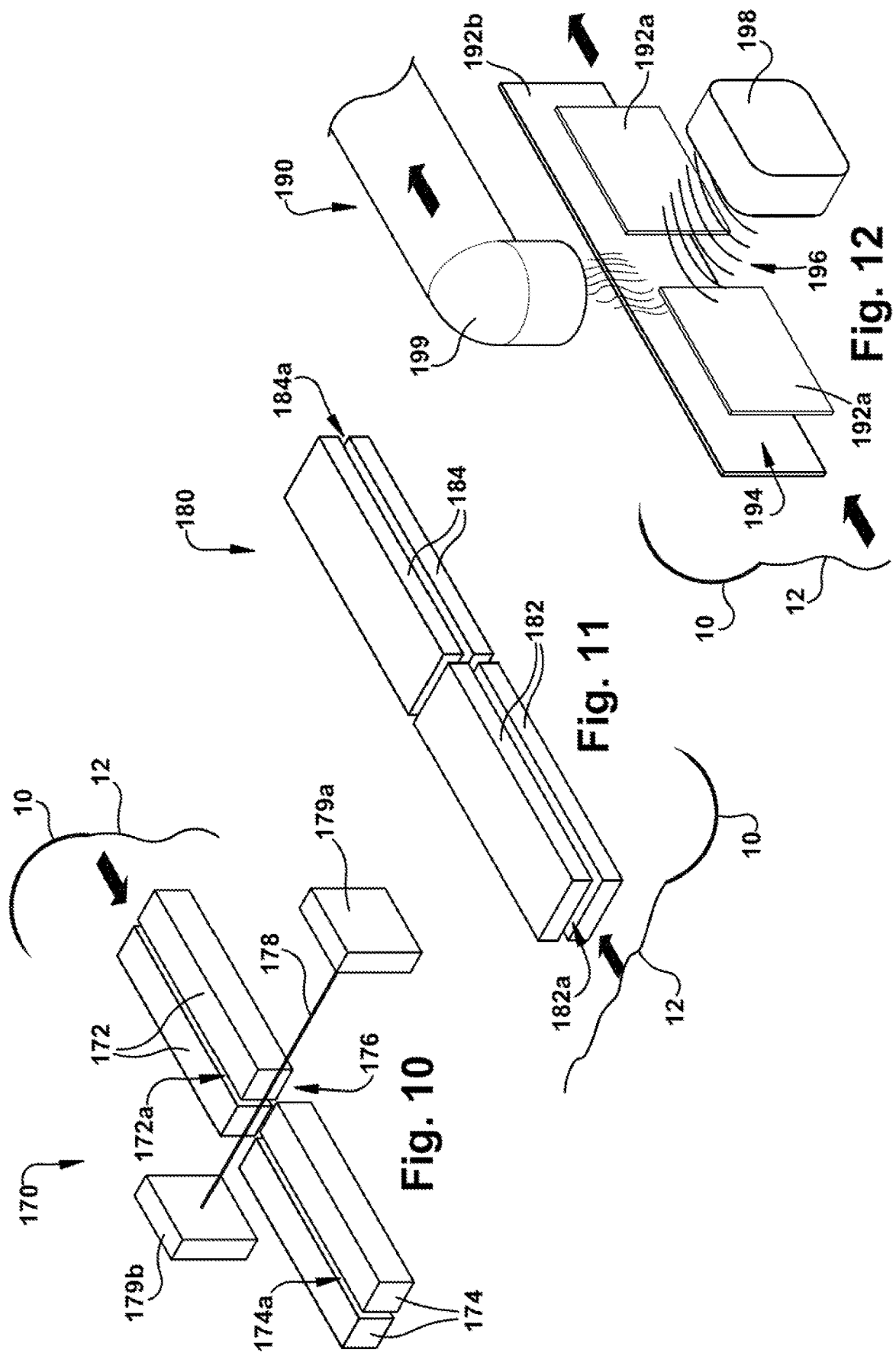

SURGICAL-IMPLEMENT COUNT AND CAPTURE SYSTEM

CROSS-REFERENCE TO RELATED APPLICATIONS

This application claims priority from U.S. provisional patent application Ser. No. 63/073,182 filed Sep. 1, 2020, the contents of which are incorporated herein by reference.

FIELD OF THE INVENTION

The present invention relates to a surgical-implement count and capture system (such as a surgical-needle count and capture system) for use in a clinical setting, and more particularly to a needle count and capture system that can be used in an operating room for collecting and counting needles used during an operating procedure.

BACKGROUND OF INVENTION

Needles and other surgical implements are used extensively during operating procedures. It is important before the patient is released from the operating room that the operating personnel account for each needle used during the operating procedure. If a needle cannot be located, then the patient must remain in the operating room, potentially with the surgical site open, until it is found. If it cannot be found outside the patient, then additional equipment, e.g., x-ray machines may be brought in to determine if and where a needle may still reside within the patient. A lost needle can result in long delays and take the operating room out of use for extended periods of time.

It is desirable to have a system that operating personnel can use to count and capture needles at the end of an operating procedure.

SUMMARY OF INVENTION

There is a provided surgical-implement count and capture system including a carrier tape having a plurality of spaced-apart receiving areas disposed longitudinally along the carrier tape. Each of the plurality of spaced-apart receiving areas is configured to receive a surgical-implement. The carrier tape is configured to follow a first pathway. A deposit station is located along the first pathway and is adapted to accommodate the deposition of a plurality of the surgical-implements respectively into successive ones of the spaced-apart receiving areas when resident at the deposit station. A counting station is located along the first pathway downstream of the deposit station. The counting station includes a sensor adapted to detect the plurality of the surgical-implements in the respective receiving areas.

There is also provided a count and capture system that includes a base station and a removable cassette reversibly installable to the base station. The removable cassette includes a cassette housing. A first reel is adapted to supply a carrier tape along a first pathway through the cassette housing. A second reel is adapted to supply a cover tape along a second pathway through the cassette housing. A third reel is adapted to receive and accumulate a capture tape that comprises portions of the carrier tape and the cover tape that have been adhered together upstream along the first pathway within the cassette housing. A deposit station is located along the first pathway and includes a deposit window in the cassette housing adapted to accommodate insertion therethrough of a plurality of surgical-implements to be deposited successively onto the carrier tape at longitudinally spaced-apart locations thereof when resident respectively in the deposit station. A counting station is located along the first pathway downstream of the deposit station. The counting station includes a counting window in the cassette housing. The base station includes a sensor adapted to penetrate the counting window when the cassette housing is installed to the base station such that the sensor is disposed adjacent to the first pathway in the counting station. The sensor is also adapted to detect the plurality of the surgical-implements deposited on the carrier tape at the respective spaced-apart locations thereof when resident in the counting station.

There is further provided a method of counting and capturing surgical-implements. The method includes steps of indexing a carrier tape comprising a plurality of receiving areas along a first pathway; depositing respective surgical-implements into successive ones of the receiving areas as each of the receiving areas is located at a deposit station located along the first pathway; detecting the respective surgical-implements in the successive receiving areas by a sensor at the counting station; and identifying or classifying the respective surgical-implements based on detecting them.

BRIEF DESCRIPTION OF THE DRAWINGS

FIG. 3A is a top view of a carrier tape used in the count and capture system of FIG. 2, illustrating needles disposed in receiving areas of the carrier tape;

FIG. 3B is a side cross-sectional view of the carrier tape of FIG. 3A taken along line 3B-3B, and showing the needles in the respective receiving areas thereof;

FIG. 3C is a side cross-sectional view as in FIG. 3B but with a cover tape applied over the carrier tape;

FIG. 4A illustrates a first embodiment of a thread cutting apparatus for the count and capture system of FIG. 1B;

FIG. 4B illustrates second embodiment of a thread cutting apparatus for the count and capture system of FIG. 1B;

FIG. 6A is a top view of the carrier tape and cover tape of FIG. 3C before a second cutting method;

FIG. 6B is a top view of a removed portion of the carrier tape and cover tape of FIG. 6A after the second cutting method;

FIG. 10 illustrates a suture trimming apparatus according to a first embodiment;

FIG. 11 illustrates a suture trimming apparatus according to a second embodiment; and FIG. 12 illustrates a suture trimming apparatus according to a third embodiment.

DETAILED DESCRIPTION OF PREFERRED EMBODIMENT

Figure 1:
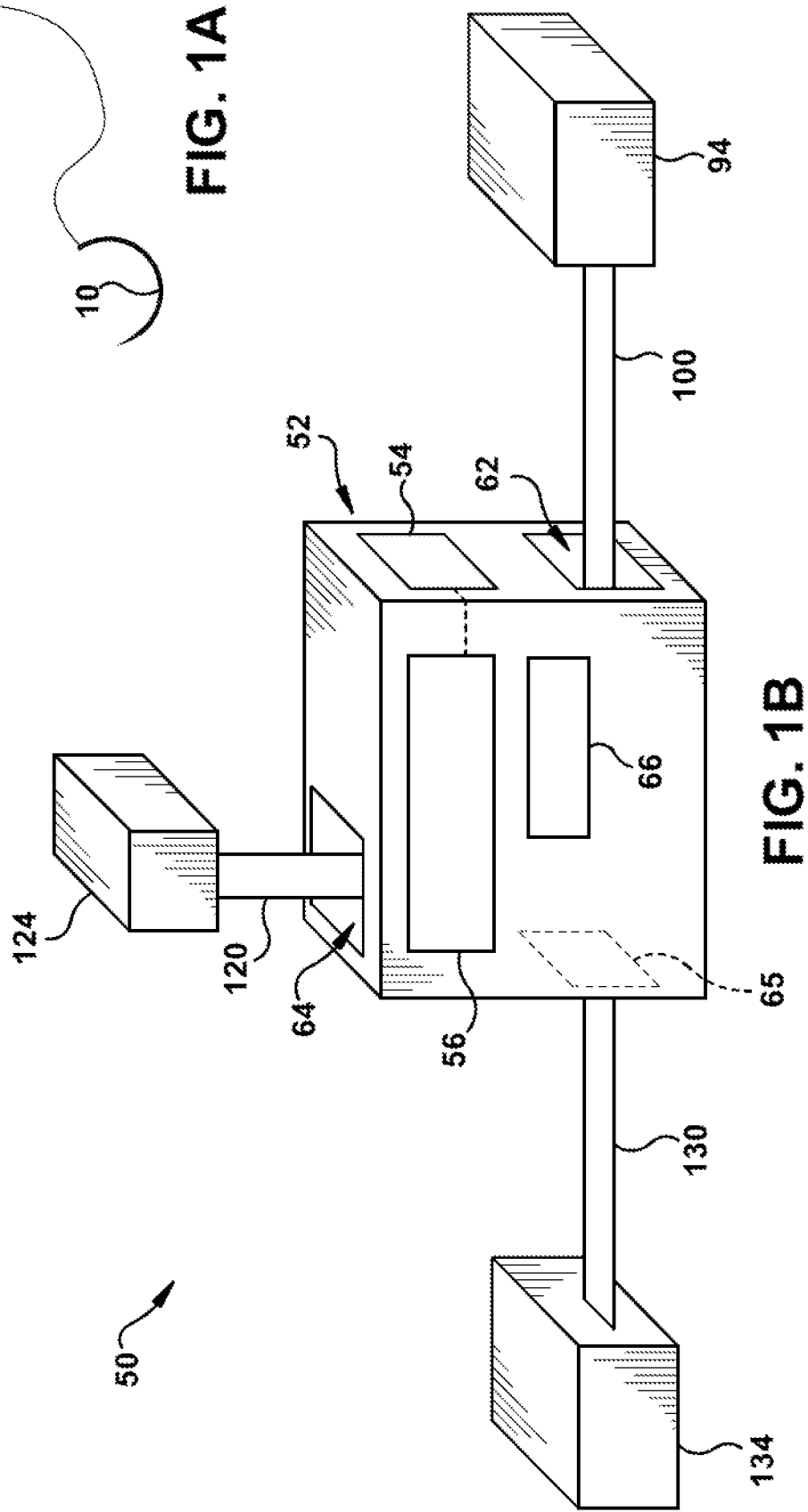
FIG. 1A illustrates an example needle used in surgery, and suture thread attached to the needle.
FIG. 1B illustrates an example surgical-implement count and capture system according to a first embodiment.

Referring to the drawings, FIG. 1A shows a needle 10 and a suture thread 12 attached to the needle 10. The needle 10 and suture thread 12 are typically used by surgeons during operating procedures.

Referring to FIG. 1B, a surgical-implement count and capture system 50 (hereinafter referred to as the "system 50") for use in a clinical setting is illustrated. The system 50 includes a main housing 52 that defines a capture and count area of the system 50. A controller 54 may be disposed in the housing 52 and connected to an input device 56. The input device 56 may include a display screen and/or a plurality of buttons (not shown) for allowing a user to control the operation of the system 50. The display screen may display information regarding the operation of the system 50 and/or may include a touch screen that allows a user to input commands to the controller 54. It is also contemplated that the input device 56 can include an output device, e.g., a printer (not shown) for printing a paper record regarding operation of the system 50 to count needles during or following a surgical procedure. It is also contemplated that the controller 54 can communicate wirelessly or via a wired connection to a central processing unit (not shown) such that data regarding the operation of the system 50 can be transmitted to the central processing unit for storage, data analysis and/or retrieval at a later time.

The housing 52 includes a carrier tape inlet opening 62 for receiving an optically clear carrier tape 100. The carrier tape 100, described in detail below, may be stored in and supplied from a first receptacle 94. The housing 52 includes a cover tape inlet opening 64 for receiving a cover tape 120. The cover tape 120, described in detail below, may be stored in and supplied from a second receptacle 124. The housing 52 also includes an outlet opening 65 from which the carrier tape 100 and the cover tape 120 together exit the housing 52 after being combined within the housing 52, as described in detail below. The combined carrier tape 100 and cover tape 120, hereinafter referred to as a capture tape 130, exits the housing 52 and is accumulated and stored within a third receptacle 134. The various openings 62, 64, 65 can be positioned on different sides of the housing 52 from what is illustrated in FIG. 1B, which is merely illustrative. It is contemplated that rollers, wheels, doctor blades, turn-bars, etc., all known in the art of conducting elongated material webs, may be used to route the carrier tape 100 and the cover tape 120 through the system 50 along desired pathways and in desired directions/orientations such that they may be combined within the housing 52 to form the capture tape 130. As illustrated, the receptacles 94, 124, 134 are spaced from the housing 52. It is contemplated that the receptacles 94, 124, 134 can be fixed or attachable to the housing 52 or even integrally formed with the housing 52 so long as the respective tapes 100, 120, 130 can be fed to or collected from the housing 52 during operation of the system 50.

Referring to FIGS. 3A-3C, the carrier tape 100 includes a plurality of receiving areas 102, that are longitudinally spaced-apart along the carrier tape 100 and are dimensioned to receive a needle 10. In an example embodiment, the receiving areas 102 can be formed as recesses disposed in the carrier tape 100 as shown in FIGS. 3A-3C. In that embodiment, the carrier tape 100 is illustrated as having square-shaped recesses when viewed from above, but it is contemplated that the recesses may have a shape other than square.

Separately, a plurality of engagement features, e.g. drive holes 104, are equally spaced-apart along one or both lateral edges of the carrier tape 100. The drive holes 104 can be engaged by pins (not shown) on drive wheels 72A, 72B (FIG. 2) of the system 50 to drive the carrier tape 100 along a pathway through the housing 52, as described in detail below. One or more optical calibration features 106 may be positioned on the carrier tape 100 to calibrate an automated counting and identification system 140 (FIG. 2), as described in detail below. In one embodiment, the calibration features 106 are circular features of predetermined size and position. These calibration features 106 can be printed on or embossed in an upper surface 100a of the carrier tape 100, and they can be of any desired size and shape. The calibration features 106 are essentially landmarks that are recognized by a camera or other sensor (described below) that allow for correlating objects such as needles 10 that are received on the carrier tape 100 with their respective receiving areas 102 on that carrier tape 100; e.g. to correlate a particular needle 10 with the associated receiving area 102. The calibration features 106 can also have known dimensions to calibrate the measurement accuracy and adjust the focus of the camera or other sensor. It is contemplated that the drives holes 104 (of known size and position) can also be used to focus the camera or sensor and/or to calibrate the measurement accuracy of the camera or other sensor, such that the drive holes 104 also can serve as calibration features.

The receiving areas 102 of the carrier tape 100 may include a collimated film 108. In embodiments where the receiving areas are provided as recesses in the tape (e.g. shown in FIG. 3B), the collimated film 108 can be disposed along the base of each recess, wherein it is configured to direct light that has passed through the carrier tape 100 in a predetermined direction, as described in detail below. During use, the needles 10 can be placed on the collimated film 108 in the respective receiving areas 102 (e.g. recess as shown in FIG. 3B).

It is contemplated that the collimated film 108 may include an adhesive, e.g. a layer or coating of PSA adhesive on its upper surface (not shown) to help secure the needles 10 to the collimated film 108. If used, the adhesive would be optically clear so as to minimally impact the light transmitted through the film on exiting the upper surface of the carrier tape 100.

Figure 2:
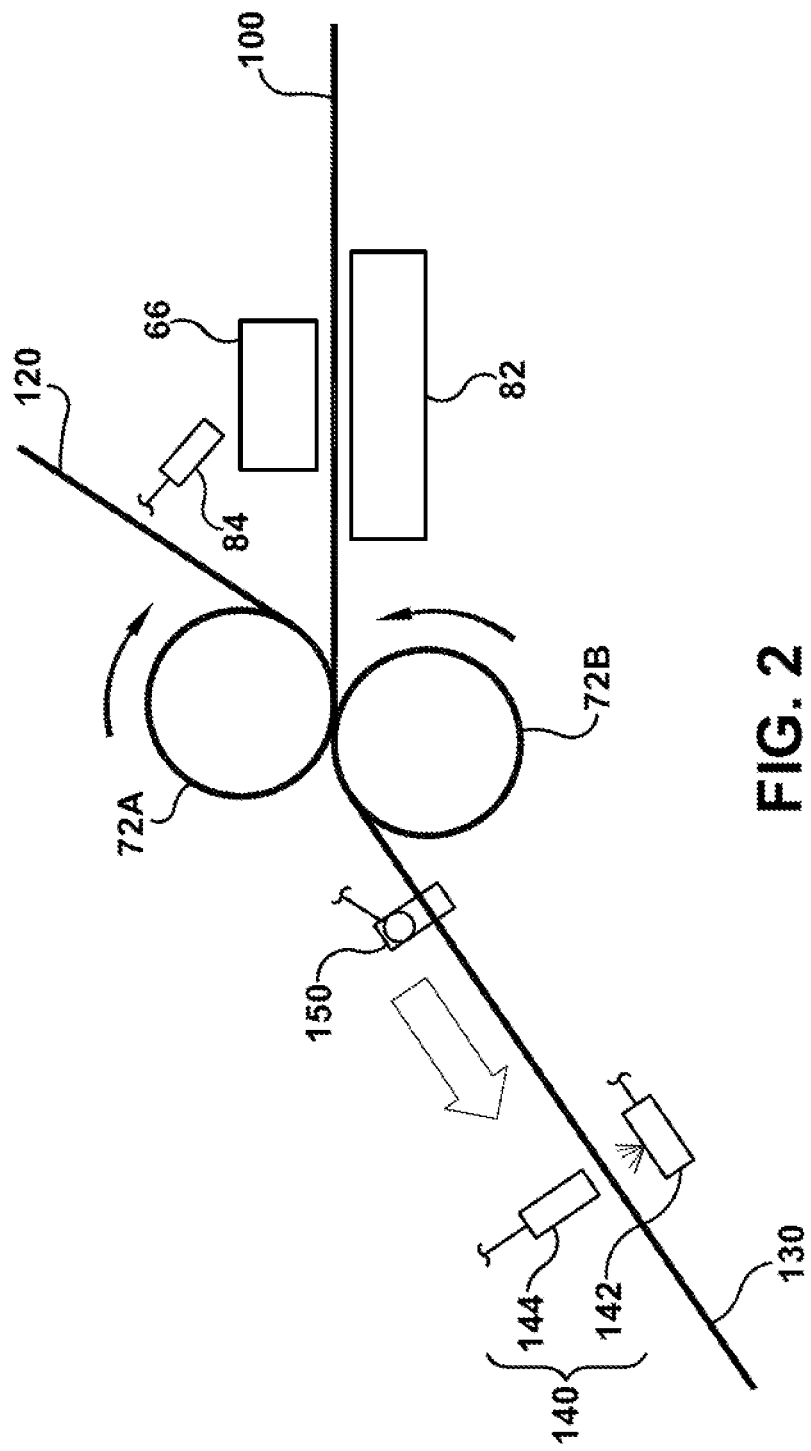
FIG. 2 is a schematic view illustrating the passage of a carrier tape for capturing surgical needles through the count and capture system of FIG. 1B.

Referring back to FIG. 1B, the housing 52 also includes a deposit window 66 through which the user may insert needles 10 for counting and capturing by the system 50. As schematically illustrated in FIG. 2, the deposit window 66 is positioned so that a needle 10 inserted through the window 66 is positioned above the carrier tape 100 when inserted by the user. The drive wheels 72A, 72B operate to index the carrier tape 100 so that a respective receiving area 102 thereof (e.g. recess as shown in FIG. 3B) is registered with (i.e. disposed at the location of) the deposit window 66 so that upon depositing a needle 10 therethrough the needle 10 will fall or may be placed in the respective receiving area 102 to be deposited and captured. That is, the deposit window 66 defines a first stationary location of the system 50 where the needles 10 are placed on the carrier tape 100. Upon deposition of a needle 10 into the adjacent receiving area 102, the drive wheels 72A, 72B can advance the carrier tape 100 to index it forward so that the next successive (still-empty) receiving area 102 comes into registry with the deposit window 66 to await a subsequent needle 10.

The optically clear cover tape 120 can be stored in and fed from the second receptacle 124 as noted above. Similar to the carrier tape 100, the cover tape 120 may include a collimated film (not shown) configured to direct light that has passed through the cover tape 120 in a predetermined direction, as described in detail below. As will be described, as the drive wheels 72A, 72B advance the carrier tape 100 to index it to the subsequent position (to bring into registry with the deposit window 66 the next successive receiving area 102, they also apply and compress thereagainst the cover tape 120 to seal each needle 10 in the respective receiving area 102 after exiting the deposit-window station.

The drive wheels 72A, 72B are operatively controlled by the controller 54 to index the carrier tape 100 (and cover tape 120). It is contemplated that the drive wheels 72A, 72B may each have their own separate motor (not shown) and independently controlled to be synchronous. Alternatively, the drive wheels 72A, 72B may be geared together via a common transmission driven by a single motor so that they synchronously turn together. The drive wheels 72A, 72B are positioned in the housing 52 for drawing the carrier tape 100 and the cover tape 120 from the receptacles 94, 124 (FIG. 1B), respectively. As described above, the drive wheels 72A, 72B can include conventional pins disposed about their circumference (not shown) configured to engage the drive holes 104 of the carrier tape 100 in a conventional manner for advancing the carrier tape 100 along its pathway into and through the housing 52. Similarly, the cover tape 120 may also include drive holes (not shown) for allowing the cover tape 120 to be drawn into the housing 52.

Alternatively, instead of using drive wheels having pins that engage with drive holes 104, the drive wheels 72A, 72B can be provided as rollers defining a nip therebetween, at which the carrier tape 100 and/or the cover tape 120 is/are compressed together by the opposing rollers and drawn through that nip as the drive wheels 72A, 72B rotate. The compressive force applied at the nip by the drive wheels 72A, 72B frictionally engages the carrier tape 100 and the capture tape 120 in order to advance them via rotation of those wheels housing. It is contemplated that the housing 52 may include additional wheels or rollers (not shown), e.g. idle wheels and rollers to align and/or direct the carrier tape 100, the cover tape 120 and the capture tape 130 through the housing 52 along desired pathways.

In the embodiment of FIG. 2, as the carrier tape 100 is drawn by the wheels 72A, 72B it passes through a deposit station, under the deposit window 66 and above a magnet 82. When the user places the needle 10 into the deposit station through the deposit window 66, the magnet 82 draws the needle 10 toward the carrier tape 100 and into a receiving area 102 (FIG. 3A) of the carrier tape 100 registered with the window 66 in that station. The magnet 82 may be an electro-magnet that can be selectively energized by the system 50 or a permanent magnet. It is also contemplated that a magnetic tape (not shown) can be attached to the lower surface of the carrier tape 100 (e.g. to underside surfaces of the base wall of the respective receiving areas 102) to draw the needles 10 into the receiving areas 102 instead of using a separate magnet 82.

An electromagnetic sensor 84 may be positioned adjacent to the deposit window 66 for detecting when a needle 10 has been placed onto the carrier tape 100. This sensor 84 can be used to enable the system 50 to detect when a needle 10 has been placed into the receiving area 102 in the deposit station (see, FIG. 3B), whereupon the controller 54 can actuate the drive wheels 72A, 72B to index the carrier tape 100. Alternatively, the user can manually provide an indication, e.g. via a button, that a needle 10 has been placed into the receiving area 102 in the deposit station, whereupon the controller 54 actuates the drive wheels 72A, 72B to index the carrier tape 100 (and the cover tape 120). It is contemplated that the receiving areas 102 in the carrier tape 100 may be spaced-apart such that indexing of the carrier tape 100 moves the receiving area 102 that just received the needle 10 to a position that it is covered by the cover tape 120, while at the same time the next-successive receiving area 102 is brought into the deposit station; i.e. in registry with the deposit window 66 so that it may receive the next-deposited needle. In this respect, once a needle 10 has been placed into a receiving area 102 in the deposit station, that receiving area 102 can be immediately sealed to enclose the deposited needle just as a subsequent receiving area 102 is positioned in the deposit station to receive the next needle 10.

Indexing of the carrier tape 100 and the cover tape 120 continues until a plurality of needles 10 are captured within the capture tape 130 formed by covering the carrier tape 100 with the cover tape 120. See FIG. 3C. Referring back to FIG. 1B, the combined carrier tape 100 and cover tape 120, forming the resultant capture tape 130, is conveyed to the third receptacle 134.

Returning to FIG. 2, before the capture tape 130 is collected by the third receptacle 134 (FIG. 1B), it passes through a counting station, which can be fixed and define a second stationary location of the system 50. In the embodiment illustrated, the counting station is downstream of the location along the pathway wherein the cover tape 120 is applied to the carrier tape 100. However, it also is contemplated that the counting station can be located upstream of that location (but still downstream of the deposit station) so that the counting station is not impacted by the cover tape 120. In the counting station, an automated counting and identification system 140 can detect and count (and optionally identify) needles 10 deposited in successive receiving areas 102 of the carrier tape 100 (now part of the capture tape 130), before exiting the housing 52 on its way to the third receptacle 134. The counting and identification system 140 may include a light source 142 that directs light through the capture tape 130 toward a sensor 144 disposed on an opposite side. The light source 142 and the sensor 144 may be controlled by the controller 54. The controller 54 may control when the light source 142 is energized and may be configured to receive information from the sensor 144 regarding the light that is detected, which is transmitted through the capture tape 130 in the vicinity of a receiving area 102 holding at least one needle 10. As described above, each receiving area 102 may include a collimated film 108 at its base, e.g. applied or deposited within the receiving area 102 on the base wall of the receiving area 102. This way, light passing therethrough and past the needle 10 can be collimated or aligned in a direction that is perpendicular to a planar expanse (e.g. to a top surface 120a—see FIG. 3C) of the cover tape 120. As noted above, it is contemplated that another collimated film (not shown) may be positioned on the top surface 120a of the cover tape 120 to aid in directing light exiting therefrom in a desired direction. In this respect, the light passing around a needle 10 disposed within a particular receiving area 102 of the cover tape 130 creates a silhouette of that needle 10 having crisp edges that may be recognized by a sensor 144 of the counting and identification system 140. In essence, the light source 142 supplies a backlight so that the sensor 144 is able to detect a collimated, coherent silhouette of the deposited needles 10. It is contemplated that a collimated film (not shown) may also (or instead) be applied directly to the light source 142 so that the light exiting the light source 142 is collimated or aligned in a direction upon exiting that source that is aligned along a desired direction; e.g. perpendicular to a planar expanse of the cover tape to which it is directed. The crisp edges of the silhouette resulting from collimation help to improve the accuracy of the sensor 144 in not only detecting needles 10 in the capture tape 130, but identifying which specific needle is present.

It is contemplated that the light source 142 may emit light of a single wavelength. The capture tape 130 may be configured so that it is some percentage (e.g. >90%) transparent to the selected single wavelength. The capture tape 130 may be selected to be opaque or substantially opaque to other wavelengths so that such other wavelengths are not transmitted to the sensor 144 of the counting and identification system 140. The ability of the counting and identification system 140 to detect or recognize accurately the needles 10 on the capture tape 130 may be improved by limiting the transmission of light of these other wavelengths to the sensor 144. For example, a filter (not shown) may be placed between the sensor 144 and the capture tape 130 to filter undesired wavelengths so that light of only the desired wavelength will reach or be detected by the sensor 144. The filter also may help to remove light from the ambient environment that could negatively impact the ability of the sensor 144 to detect or recognize accurately the needles 10. The filtering of light also may help the counting and identification system 140 distinguish between the needle 10 and the suture thread 12 attached to it. It is contemplated that as the light of the desired wavelength passes the needle 10 and the suture thread 12, the difference in the materials of the needle 10 and the suture thread 12 may be result in two distinct images that can be distinguished by the counting and identification system 140.

It is also contemplated that the capture tape 130 may be tinted or colored to filter undesired wavelengths, e.g. to transmit only light of the selected single wavelength; or at least to reduce transmission of light of other wavelengths. This further reduces the likelihood that light of other wavelengths will be transmitted to the sensor 144 to negatively impact the ability of the counting and identification system 140 to detect or recognize accurately the needles 10 in the capture tape 130. After the capture tape 130 has passed the counting and identification station where the identification system 140 counts needles, it may be advanced to the third receptacle 134 (FIG. 1B) for storage.

It is to be noted that the counting and identification system 140 need not include the light source 142 located on the opposite side of the carrier tape 100 from the sensor 144. Instead, the light source 142 may be located on the same side of the carrier tape 100 as the sensor 144 to illuminate the carrier tape 100 and the needle 10. In this case the sensor 144 detects light reflected from the carrier tape 100 (and a present needle 10) in order to identify that needle, rather than transmitted light as in the earlier-described embodiment. It is contemplated that the light source 142 can emit ultraviolet light or more other wavelengths that can be differentially absorbed or reflected by the needle 10 and the suture thread 12 to aid in the ability of the counting and identification system 140 to distinguish between the needle 10 and the suture thread 12. It is further contemplated that the sensor 144 can be a video camera that captures successive images of the needle 10 as it passes the counting and identification system 140.

It is also contemplated that the counting and identification system 140 can position light sources 142 on both sides of the carrier tape 100. It is also contemplated that the counting and identification system 140 can include multiple light sources 142 on one or both sides of the carrier tape 100 to minimize shadows and improve the accuracy of the sensor 144 in detecting the needle 10. It is also contemplated that the multiple light sources 142 can have different wavelengths/colors and the multiple light sources 142 can be sequentially energized to detect the needles 10 using the different wavelengths/colors. The counting and identification system 140 can combine image information from the different wavelengths/colors to improve the accuracy of the system 140 in detecting the needles 10.

The counting and identification system 140 can be configured to include software that is programmed to recognize or classify the type and number of needles 10 in the capture tape 130 based on the shape of their respective silhouettes. The counting and identification system 140 may be configured such that movement of the capture tape 130 relative to the sensor 144 may aid in improving the accuracy of the sensor 144. The movement of the capture tape 130 may aid the counting and identification system 140 in recognizing the needle 10 by presenting the needle 10 at different angles from which its silhouette will be perceived by the sensor 144. For example, the sensor 144, which may be fixed, can take silhouette images of the needle(s) 10 from more than one perspective where the relationship of those perspectives is known or fixed. By combining image information from multiple perspectives, software can be programmed to construct a composite 3D image of the particular needle(s) 10 in order to match them precisely with the number and type known to have been used during surgery—similar to how the human brain constructs 3D images based on combining the perspectives from the left and right eyes. This shift in angle to capture multiple images from different perspectives, can help the counting and identification system 140 improve its recognition of the needle 10. It is also contemplated that instead of a single sensor 144 that takes multiple images of the needle 10, that multiple sensors 144 can be used wherein each sensor 144 takes an image of the needle 10 from a different perspective. These multiple perspectives are then combined to construct a 3D image of the needle 10, as described above.

As noted above, the optical calibration features 106 provide the counting and identification system 140 with a feature of known size and position. Once the counting and identification system 140 detects the calibration feature 106 it may use the known size and position of the calibration feature 106 to determine the size and position of the needles 10 in the capture tape 130. The frequency of the calibration procedure may be programmed into the counting and identification system 140, e.g. each time a carrier tape 100 is placed in the system 50, once per operating procedure, based on time of use, etc.

As described above, the sensor 144 may be configured to detect the silhouette of the needles 10. The controller 54, or optionally a separate processor, can algorithmically classify the gathered data (e.g. using artificial intelligence) or compare the detected silhouette shape against silhouette data corresponding to a plurality of different needles 10 stored in a memory coupled to the controller (processor), and thereby identify the particular needle that has been deposited. If the controller (processor) is preprogrammed with all needles 10 that are to be used in a particular procedure, or if specific needles are programmed as they are consumed during a procedure, then the silhouette record can be utilized to account for the needles 10 used. This will help ensure that all such needles 10 are accounted for when the procedure is over and before discharging the patient from the operating room. Moreover, the system can account for quantities of different categories (e.g. types and styles) of needles 10 based on their unique silhouettes, in order to track the different needles 10 used and accounted for at the end of the procedure.

As illustrated in FIG. 1A, a suture thread 12 is often connected to a surgical needle 10. In some instances, a user may trim the suture thread 12 from the needle 10 before depositing the needle into the deposit window 66.

Referring to FIGS. 10-12, different embodiments of a suture trimming system 170, 180, 190 are illustrated. It is contemplated that the suture trimming system 170, 180, 190 can be located on an external side wall of the system 50 so that a user has easy access to the suture trimming system 170, 180, 190. It is also contemplated that the suture trimming system 170, 180, 190 can be a component that is remote from the system 50 or one that is selectively attachable to the system 50.

Referring to FIG. 10, the suture trimming system 170 includes first suture guides 172 and second suture guides 174 that are spaced apart to define a trimming area 176. Each guide 172, 174 defines a guide slot 172a, 174a, respectively, for receiving the suture thread 12 (i.e. suture tail 12a) to be trimmed. A wire 178 extends through the trimming area 176. Opposite ends of the wire 178 are connected to an electric source 179a, 179b for applying an electric current to the wire 178. The wire 178 is made from a material that is selected so that the application of the electric current to the wire 178 causes the wire 178 to increase to a sufficient temperature to cut the suture thread 12 upon contact. The suture guides 172a, 174a are positioned to align with each other such that as the suture thread 12 passes through the trimming area 176 from one of the guides 172, 174 to the other of the guides 172, 174 (see, e.g., the arrow in FIG. 12) the suture thread 12 is cut by the wire 178 upon contact.

Referring now to FIG. 11, the trimming system 180 includes a first pair of sponges 182 and a second pair of sponges 184. The first pair of sponges 182 are spaced-apart to define a first elongated slot 182a between them. Similarly, the second pair of sponges 184 are spaced-apart to define a second elongated slot 184a between them. The slots 182a, 184a are dimensioned to ensure that the suture thread 12 contacts the surfaces of the respective sponges 182, 184 as it passes through the slots 182a, 184a. The first pair of sponges 182 can be saturated with a liquid that dissolves the suture thread 12, e.g., known nylon solvents such as 100% acetic acid, bromine liquid, calcium chloride, 15% calcium hypochlorite, 50-100% carbolic acid, formic acid, 5% phenol or resorcinol. The second pair of sponges 184 can be dry.

During use, a user passes the needle 10 and the suture thread 12, in particular, the junction where the needle 10 and the suture thread 12 are connected together, through the first elongated slot 182a such that the suture thread 12 is coated with the liquid in the first pair of sponges 182. The suture thread 12 then passes through the second elongated slot 184a to remove excess liquid via the dry sponges. As noted above, the liquid on the first pair of sponges 182 is selected to dissolve the suture thread 12. After a period of time sufficient for the liquid to react with the suture thread 12, the user may remove the suture thread 12 from the needle 10 and place needle 10 in the receiving area 102 of the carrier tape 100, as described in detail above.

In an alternative embodiment, the first pair of sponges 182 is saturated with an ultraviolet (UV) fluorescent dye. In this embodiment, the user does not remove the suture thread 12 but places the needle 10 and the suture thread 12 into the receiving area 102 of the carrier tape 100, as described in detail above. The UV fluorescent dye is selected to bind to the suture thread 12 but not to the needle 10. The counting and identification system 140 can include a UV light that illuminates the UV fluorescent dye coated on the suture thread 12 so the counting and identification system 140 can distinguish between the needle 10 and the suture thread 12. This enables the counting and identification system 140 to recognize and characterize the needle 10 based on its shape and size without regard to the attached suture thread 12, which can be distinguished from the needle 10 based on the illuminated UV fluorescent die bound thereto.

Referring now to FIG. 12, the suture trimming system 190 includes a first plate 192a and a second plate 192b that are spaced-apart to define an elongated opening 194 therebetween. The first plate 192a includes an opening that defines a trimming area 196 of the system 190. (In the embodiment shown, the first plate 192a can be provided as two distinct plates separate from one another in a common plane to define the trimming area 196 therebetween. Alternatively it can be a single plate with a window formed therein to define that area 196). A heater 198, e.g. an infrared heat source, a flame, etc. is positioned adjacent to the trimming area 196 and oriented to direct heat into the trimming area 196. The heater 198 can be configured to supply heat at a sufficient intensity to burn or pyrolyze the suture thread 12 while not damaging the needle 10. An exhaust duct 199 is positioned above the trimming area 196 for exhausting fumes from the trimming area 196 during operation.

During use, the user passes the needle 10 and suture thread 12 through the elongated opening 194 to the trimming area 196. Once in the trimming area 196, the heating device 198 (either based on detection of the needle 10 by a sensor (not shown) or by command from the user) directs heat into the trimming area 196 to burn/pyrolyze the suture thread 12. The exhaust duct 199 is configured to draw air and combustion by-products from the trimming area 196. Once the suture thread 12 has been eliminated, the user may place the needle 10 into the receiving area 102 of the carrier tape 100, as described in detail above.

In an alternative embodiment, the heater 198 can be a scanning laser that repeatedly passes laser light through the trimming area 196. The power of the laser can be selected to burn/pyrolyze the suture thread 12 while not damaging the needle 10. It should be appreciated that the needle 10 may reflect the laser light while the suture thread 12 absorbs the delivered energy and is burned/pyrolyzed.

Referring to FIG. 2, in instances where the user is not required or unable (or chooses not) to trim the suture thread 12, either manually or using one of the foregoing suture trimming systems 170, 180, 190, the system 50 can include an automated thread cutting system 150 that is positioned upstream of the automated counting and identification system 140 along the travel pathway of the capture tape 130, and downstream of the drive wheels 72A, 72B. The automated thread cutting system 150 is configured for trimming the suture thread 12.

Figure 5A:
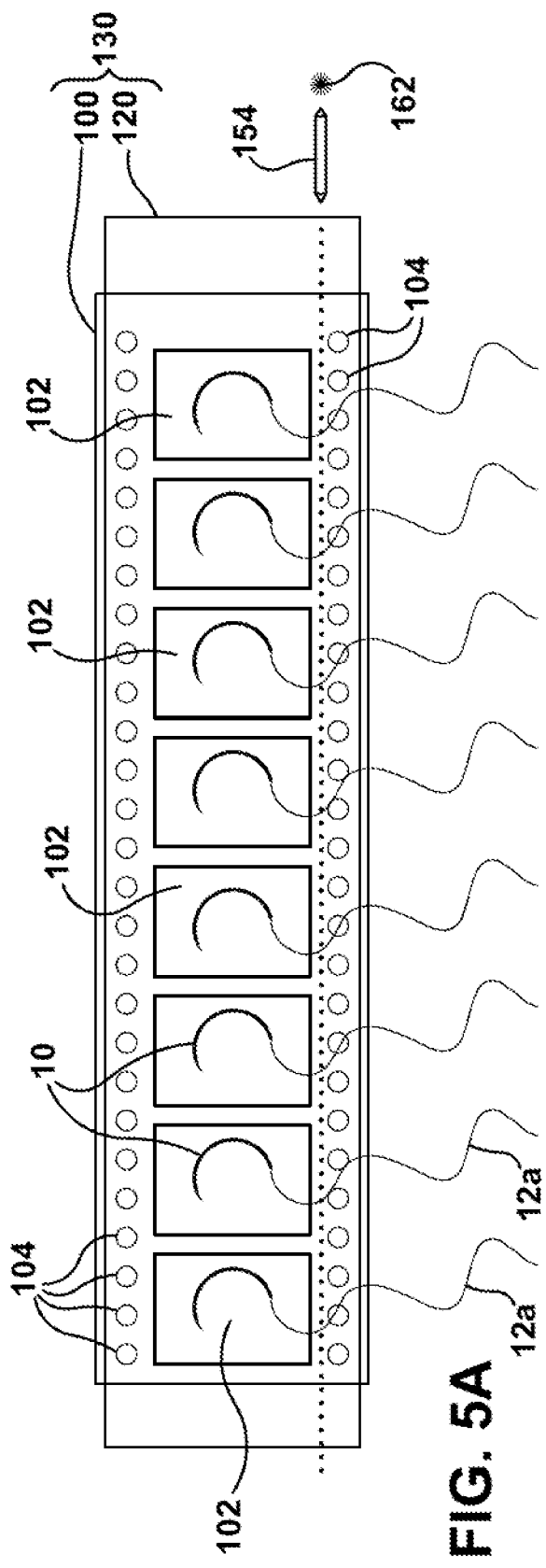
FIG. 5A is a top view of the carrier tape and applied cover tape of FIG. 3C before a first cutting method.
Figure 5B:
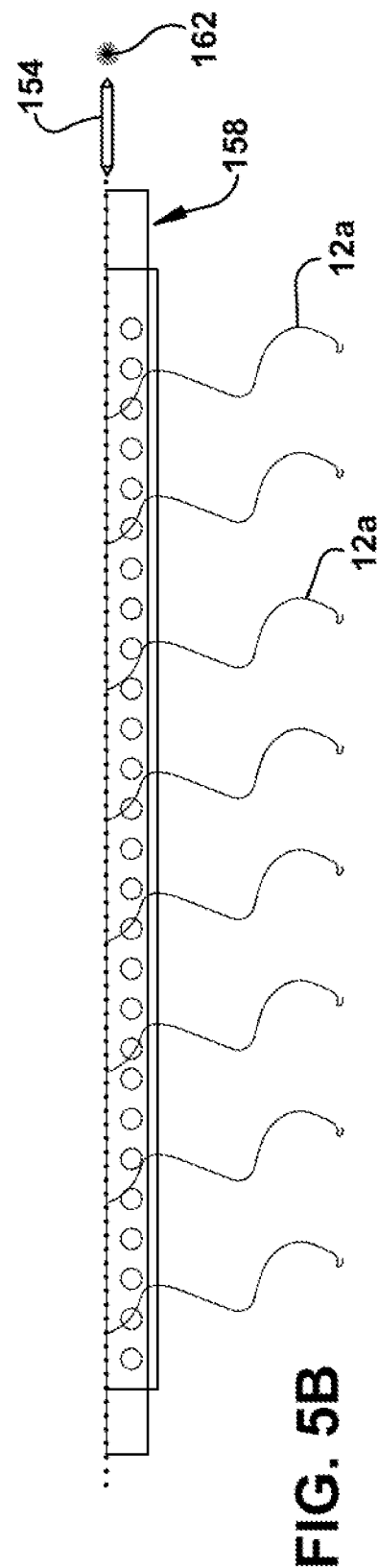
FIG. 5B is a top view of a removed portion of the carrier tape and cover tape of FIG. 5A after the first cutting method.

When a needle 10 is received in a receiving area 102 of the carrier tape 100, which is then covered by the cover tape 120, a residual portion of a suture thread 12 affixed to the needle (i.e. a suture tail 12a) may be sandwiched between the opposing carrier- and cover tapes 100 and 120 so that a terminal end thereof extends from an edge of the resulting capture tape 130 (see, e.g. FIG. 5A). Referring to FIG. 4A, the thread cutting system 150 may include guides 152 that are positioned and configured to direct a portion of the suture tail 12a extending from the capture tape 130 toward a cutter wheel 154. The cutter wheel 154 may be attached to a motor 156 whose operation is controlled by the controller 54. The motor 156 is configured to rotate the cutter wheel 154 to cut the suture tail 12a adjacent to where it emerges from the capture tape 130, optionally together with an edge portion of that capture tape 130 yielding a scrap strip 158. For example, as illustrated in FIGS. 5A and 5B, in one embodiment the cutter wheel 154 is positioned to cut a portion of the capture tape 130 at the same time that is cuts the suture tail 12a. By cutting both the suture tail 12a and the capture tape 130 together, the cutter wheel 154 captures the excess suture tail 12a in the scrap strip 158 that is severed from a lateral edge of the capture tape 130. The scrap strip 158 may be collected in a receptacle for ease of disposal.

In the embodiment illustrated in FIGS. 5A and 5B, the cutter wheel 154 is positioned to cut the capture tape 130 along a cut line 159a to remove the drive holes 104 that extend along one side of the capture tape 130 at the same time that the suture tail 12a is cut. Thus, the adjacent drive holes 104 now will be embodied in the resulting scrap strip 158. These drive holes 104 may be used by other drive wheels (not shown) of the system 50 for conveying the scrap strip 158 to a trash receptacle (not shown). In an alternative embodiment, illustrated in FIGS. 6A and 6B, the cutter wheel 154 may be positioned at a cut line 159b to remove only a lateral-most portion of the capture tape 130 with the cut suture tails 12a, leaving the adjacent drive holes 104 intact in the capture tape 130. The resulting scrap strip 158 again may be collected in the trash receptacle (not shown).

In another embodiment, illustrated in FIG. 4B, the cutter wheel 154 is replaced by a laser 162 to cut the suture thread 12 and/or the capture tape 130. In a manner similar to that described above for the cutter wheel 154, the laser 162 may be positioned at various locations between the opposing lateral edges of the capture tape 130 for cutting the capture tape 130 at a desired location.

In summary, referring to FIG. 2, during operation the system 50 is configured to attach the cover tape 120 to the carrier tape 100 after a needle 10 has been placed in the receiving area 102 (FIG. 3A) of the carrier tape 100. The needle 10 is placed into the receiving area 102 (FIG. 3A) at the first stationary location (e.g. at a deposit station, through the deposit window 66) and thereafter it is captured in the carrier tape 100 by the cover tape 120. The carrier tape 100 and the cover tape 120, now referred to as the capture tape 130, can be conveyed past the thread cutting system 150 so that emergent suture tails 12a may be trimmed from the capture tape 130, with or without a scrap strip 158 being trimmed from a lateral edge of the capture tape 130. After trimming, the capture tape 130 passes the second stationary location (e.g. the aforementioned counting station) where the counting and identification system 140 identifies and counts the needles 10 in the capture tape 130. After counting, the capture tape 130 may be collected for storage and/or disposal. As noted above, it is also contemplated that the counting and identification system 140 may be located upstream of the location where the cover tape 120 is applied to the carrier tape 120. In this location, detection of needles (or other surgical implements) in the counting and identification system 140 will not be impacted by cover tape 120 because there will be none present. Thereafter, once the needles 102 are detected and counted at the counting station, the cover tape 120 may be applied to the carrier tape 100.

Figure 7:
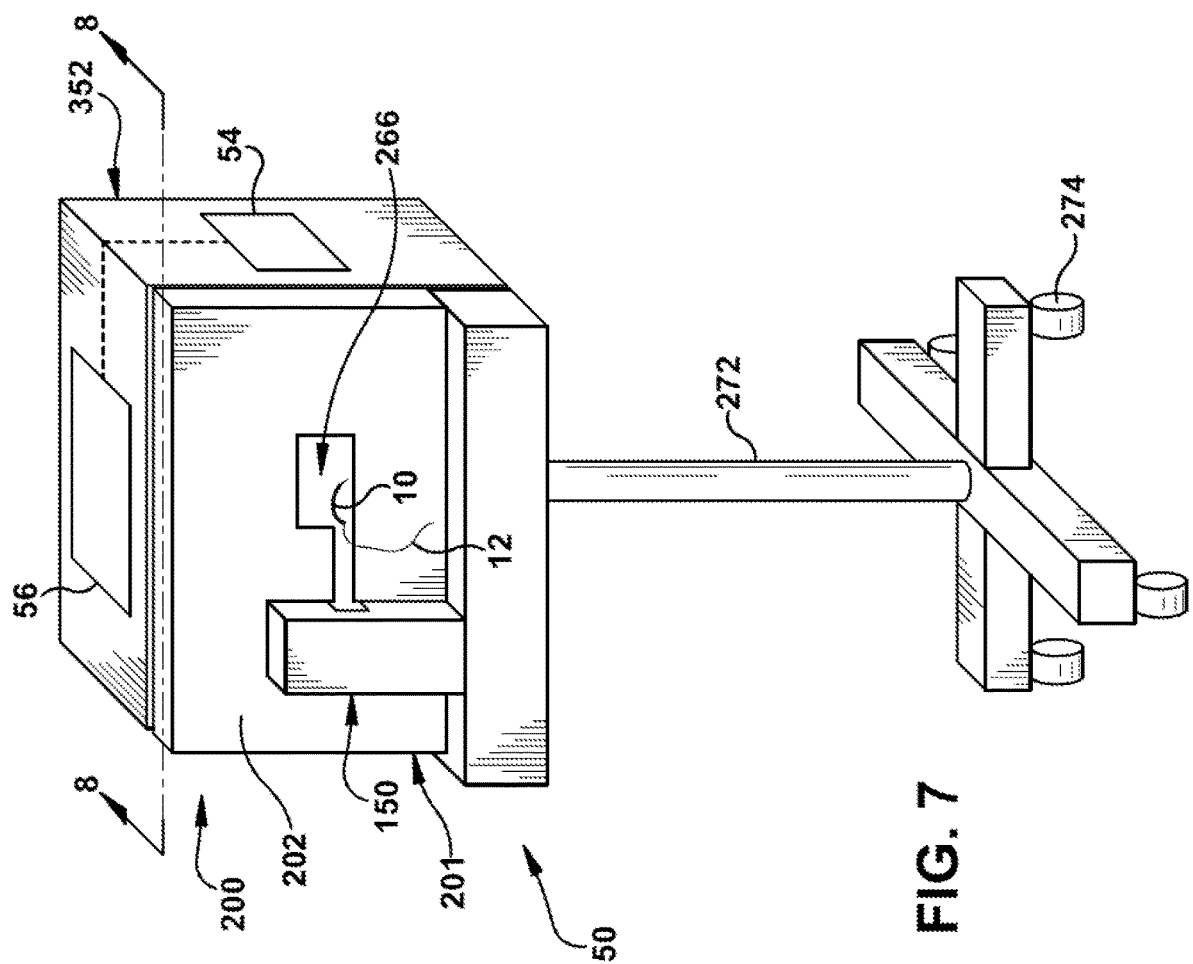
FIG. 7 illustrates a mobile needle count and capture system accordingly to a second embodiment, including a replaceable cassette for holding used surgical needles counted by the system.
Figure 8:
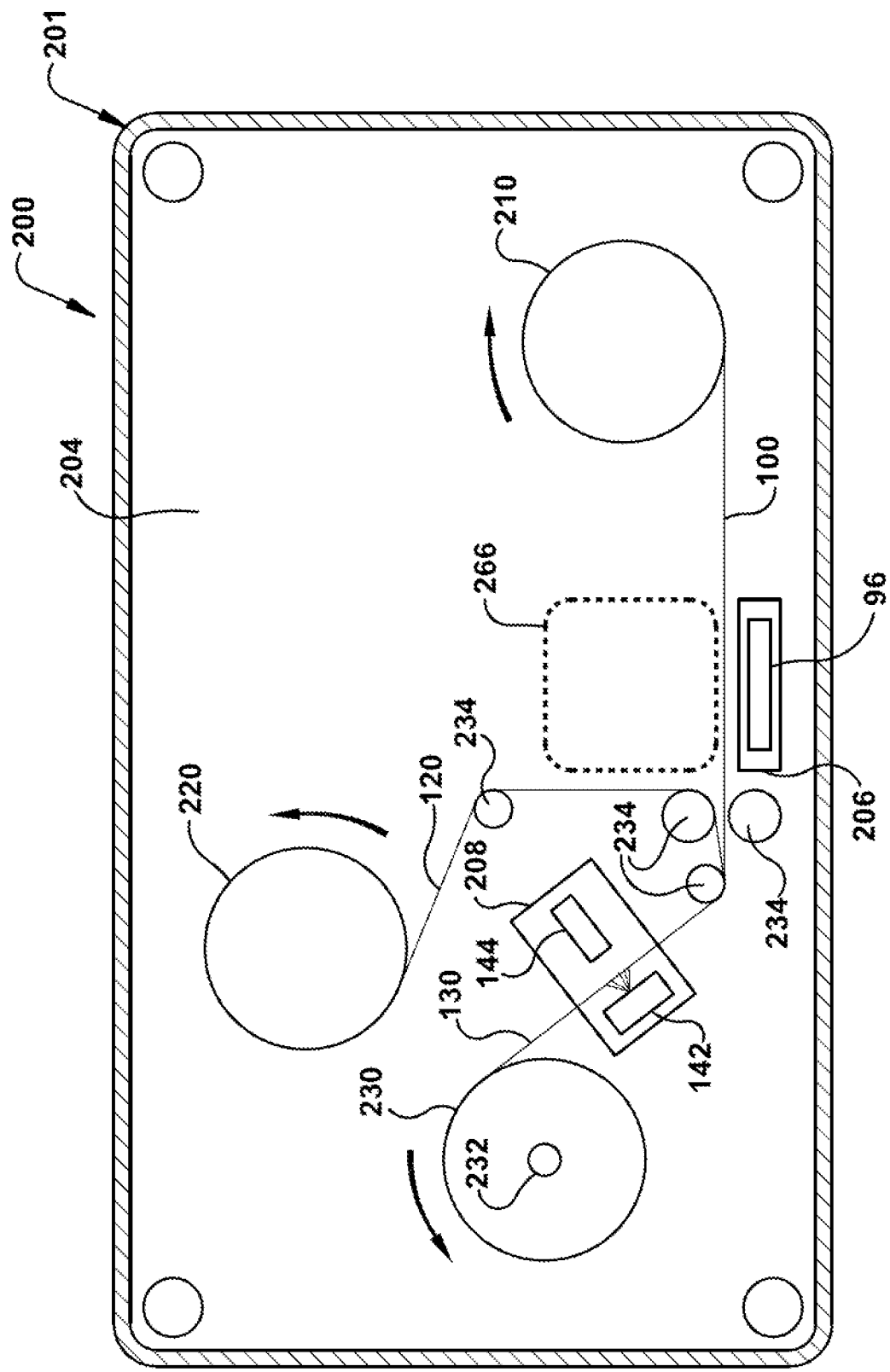
FIG. 8 is a sectioned schematic view of the replaceable cassette for use with the count and capture system of FIG. 7 taken along line 8-8.

According to another embodiment, illustrated in FIGS. 7-9, the system 50 includes a removable cassette 200 wherein the carrier tape 100, the cover tape 120 and the capture tape 130 are all disposed within an internal cavity of a cassette housing 201 of the cassette 200. The cassette 200 is configured to be installed to or inserted into a base station 352. Referring to FIG. 7, the cassette 200 is shown disposed between the base station 352 and the thread cutting system 150. It is contemplated that the thread cutting system 150 may be displaceable relative to the base station 352 to accommodate insertion of the cassette 200 to be attached to the base station 352, as described in detail below.

The front wall 202 of the cassette housing 201 includes a deposit window 266 configured to allow a user to insert needles 10 into the cassette 200. The deposit window 266 is located in a similar manner as described above for the deposit window 66 in the previous embodiment. In other words, the deposit window 266 allows the user access to the carrier tape 100 at a deposit station for needles so the user can place a needle 10 into a receiving area 102 of the carrier tape 100 temporarily located in that station.

Referring to FIG. 8, a rear wall 204 of the cassette housing 201 includes a magnet window 206 to accommodate insertion therein of a magnet 96 affixed to or as part of the base station 352 when the cassette 200 is installed, so that the magnet 96 extends into the cassette housing 201 at a location below the carrier tape 100 adjacent to the deposit window 266 (i.e. in the deposit station). As described in detail above, the magnet 96 helps to hold a needle 10 in the receiving area 102 of the carrier tape 100 when placed in the deposit station by the user. A counting window 208 is formed in the rear wall 204 and is positioned to allow the light source 142 and the sensor 144 of the automated counting and identification system 140 also to be inserted within the cassette housing 201 when installed to the base station 352, at an appropriate location to define the counting station in that cassette 200.

The cassette 200 includes first, second and third reels 210, 220, 230 wherein the carrier tape 100 is wound on and supplied from the first reel 210, the cover tape 120 is wound on and supplied from the second reel 220 and the capture tape 130 is collected on the third reel 230. The cassette 200 can include a plurality of idle wheels 234 for directing the various tapes 100, 120, 130 along desired paths within the cassette 200.

The third reel 230 includes a geared or toothed opening 232 accessible from outside the rear wall 204 and configured to engage a drive sprocket 53a (FIGS. 9A and 9B) extending from the housing 52. When the cassette 200 is attached to the base station 352 the drive sprocket 53a (FIGS. 9A and 9B) extends into and engages the geared or toothed opening 232. The drive sprocket 53a (FIGS. 9A and 9B) is attached to a motor (not shown) that is controlled by the controller 54. When energized, the motor causes the drive sprocket 53a (FIGS. 9A and 9B) to turn, which drives the third reel 230 causing it to rotate in order to collect and accumulate the capture tape 130 thereon. As the third reel 230 rotates, tension is applied to the carrier tape 100 and the cover tape 120 thereby drawing them from the reels 210, 220, respectively, which themselves may engage respective sprockets 53b that extend from the housing 52. The sprockets 53b may be idle sprockets that serve only to support smooth rotation of the reels 210 and 220 as their respective tapes are drawn therefrom via rotation of the third reel 230 downstream. In this embodiment, tension applied by the drive sprocket 53a (FIGS. 9A and 9B) draws the carrier tape 100 and the cover tape 120 from the first and second reels 210, 220, respectively, through the cassette 200 to the third reel 230 where the capture tape 130 is wound around the third reel 230. Alternatively, the sprockets 53b also may be driven, in which case their rotations will be controlled to issue the respective carrier- and cover tapes 100 and 120 at rates substantially equal to the take-up rate of the capture tape 130 on the third reel 230.

Figure 9B:
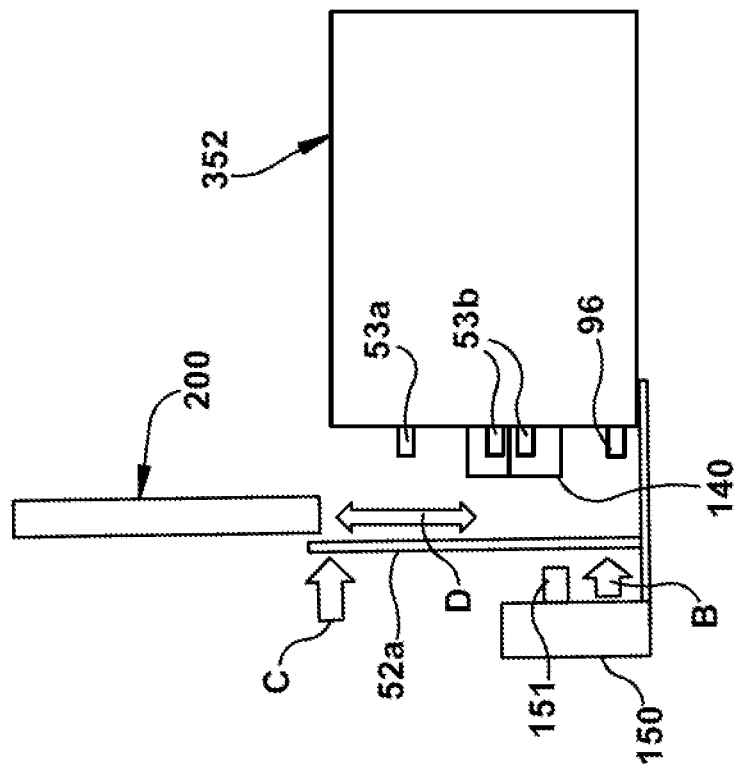
FIG. 9B is a schematic side view showing a door for connecting the cassette of FIG. 8 to the count and capture system of FIG. 7 according to a second embodiment.
Figure 9A:
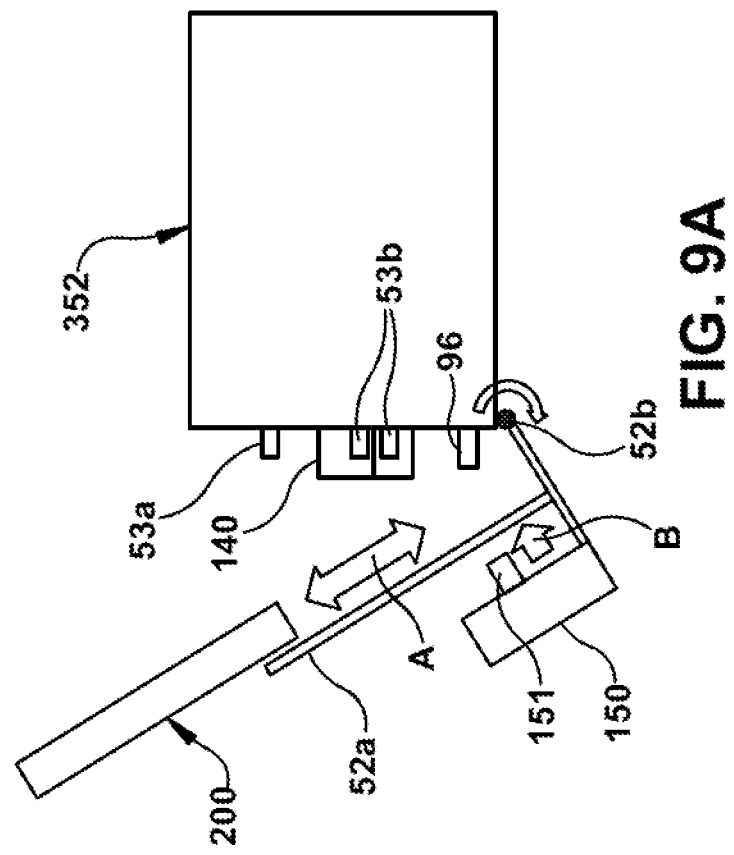
FIG. 9A is a schematic side view showing a door for connecting the cassette of FIG. 8 to the count and capture system of FIG. 7 according to a first embodiment.

Referring to FIGS. 9A and 9B, the cassette 200 may be attached to the base station 352 using a variety of methods. For example, referring to FIG. 9A, the cassette 200 can be inserted along a door 52a of the base station 352 in direction A. After the cassette 200 is inserted, the door 52a and the cassette 200 are pivoted about a pivot point 52b toward a front of the base station 352. As the cassette 200 pivots toward the base station 352, the drive sprocket 53a engages the geared or toothed opening 232 (FIG. 8) of the third reel 230, the sprockets 53b engaged the respective first reel 210 and second reel 220, the magnet 96 extends into the magnet window 206 and the automated counting and identification system 140 extends into the counting window 208 of the cassette 200.

Thereafter, the thread cutting system 150 is slid towards the cassette 200 in a direction B and positioned so that a portion 151 of the thread cutting system 150 extends into the deposit window 266. This portion 151 may include the cutter wheels 154 or the laser 162 (described in detail above) and position the respective component for trimming the suture tail 12a and/or the capture tape 130. As described above, the cassette 200 is captured between the thread cutting system 150 and the base station 352 of the system 50. Once the cassette 200 is secured to the base station 352, the system 50 may be operated as described in detail above for the previous embodiment except that the carrier tape 100, the cover tape 120 and the capture tape 130 are now all retained within the cassette 200.

In a second embodiment illustrated in FIG. 9B, the door 52a slides only in a direction C relative to the base station 352. Once the cassette 200 is inserted into the door 52a (along direction D) and positioned adjacent the base station 352, the aforementioned components, i.e., the drive sprocket 53a, the sprockets 53b, the magnet 96 and the automated counting and identification system 140 engage the cassette 200 similarly as described above. Thereafter, the thread cutting system 150 is moved towards the cassette 200 (in direction B) in a manner similar to that described above for FIG. 9A. In either the embodiment of FIG. 9A or 9B, the cassette 200 constitutes a fixed-capacity cartridge for collecting a plurality of surgical needles, and collecting them within a removable (and optionally disposable) cassette. The cassette with needles therein may be retained as long as desired, e.g. until after the patient is discharged and/or for auditing purposes. Once it is no longer needed as part of the record of a surgical procedure, the cassette can be discarded as a whole, including the captured needles therein.

The embodiments of the count and capture system 50 illustrated in FIG. 2 may be a table-top unit. Referring to FIG. 7, in an alternative embodiment the system 50 may be a floor-standing unit that is supported above the floor by a stand 272 having wheels 274 for allowing the system 50 to be moved by a user.

Although the aforementioned embodiments have been described with respect to surgical needles, it will be appreciated that those embodiments also may be utilized to account for and keep track of other surgical-implements used during any surgical procedure, such as surgical sponges, clamps, or other conventional surgical instrumentalities, that can be capture on a tape so that their respective silhouettes can be detected by a camera or other sensor to identify and account for them.

Although the invention has been described with respect to select embodiments, it shall be understood that the scope of the invention is not to be thereby limited, and that it instead shall embrace all modifications and alterations thereof coming within the spirit and scope of the appended claims.

What is claimed:

1. A surgical-implement count and capture system comprising:
   a base station and a cassette removably installable to the base station, the cassette comprising:
      a carrier tape having a plurality of predefined, spaced-apart receiving areas disposed longitudinally along the carrier tape, each of said plurality of spaced-apart receiving areas being configured to receive a surgical-implement, the carrier tape following a first pathway;
      a deposit station located along said first pathway and adapted to accommodate deposition of a plurality of said surgical-implements respectively into successive ones of said spaced-apart receiving areas when resident at the deposit station;
      a cover tape following a second pathway that intersects the first pathway downstream of the deposit station such that the cover tape can be applied to the carrier tape to capture the surgical-implements in the respective receiving areas; and
      a counting station located along said first pathway downstream of said deposit station; and
   the base station further comprising a sensor adapted to detect said plurality of said surgical-implements in the respective receiving areas when the cassette is installed to the base station.

2. The count and capture system of claim 1, said plurality of said surgical-implements being surgical needles.

3. The count and capture system of claim 1, said carrier tape comprising an engagement feature adapted to facilitate driving the carrier tape along the first pathway.

4. The count and capture system of claim 1, said carrier tape comprising an optical calibration feature comprising a landmark of predetermined size and location that is detectable by said sensor.

5. The count and capture system of claim 1, said carrier tape being tinted or colored to filter light of undesired wavelengths.

6. The count and capture system of claim 1, further comprising an adhesive disposed on at least one of said plurality of spaced-apart receiving areas and adapted to adhere said surgical-implement to the at least one receiving area.

7. The count and capture system of claim 1, further comprising a magnetic sheet attached to a lower surface of the carrier tape below at least one of said plurality of spaced-apart receiving areas.

8. The count and capture system of claim 1, further comprising a light source opposing the sensor relative to said first pathway for emitting light through said carrier tape toward said sensor.

9. The count and capture system of claim 8, further comprising a collimated film disposed on said light source for directing light exiting said light source in a direction perpendicular to a planar expanse of said carrier tape.

10. The count and capture system of claim 8, further comprising a collimated film disposed on at least one of said plurality of spaced-apart receiving areas for directing light exiting an upper surface of the at least one receiving area in a direction perpendicular thereto.

11. The count and capture system of claim 1, said sensor being adapted to detect silhouettes of said plurality of surgical-implements.

12. The count and capture system of claim 1, further comprising:
a processor adapted to identify and count said plurality of surgical-implements collected the respective receiving areas based on signals from said sensor.

13. The count and capture of claim 1, wherein the base station further comprises:
a magnet adapted to penetrate a magnet window of the cassette when the cassette housing is installed to the base station, said magnet configured to apply a magnetic force to retain a said surgical-implement against said receiving area when resident in the deposit station.

14. The count and capture of claim 1, further comprising:
an electromagnetic sensor at said deposit station and adapted to detect a presence of a said surgical-implement placed on said carrier tape at said deposit station.

15. The count and capture system of claim 1, further comprising:
a first source adapted to supply the carrier tape along the first pathway;
a second source adapted to supply a cover tape along a second pathway that intersects the first pathway downstream of the deposit station; and
a receptacle adapted to receive and accumulate a capture tape that comprises said cover tape applied to the carrier tape, the receptacle being located at an end of said first pathway.

16. The count and capture system of claim 15, wherein the cassette contains said first source, said second source and said receptacle, wherein the first source is a first reel having an unused portion of said carrier tape wrapped thereon, the second source is a second reel having an unused portion of said cover tape wrapped thereon, and the receptacle is a third reel onto which the capture tape is wound to accumulate it.

17. The count and capture system of claim 1, wherein said plurality of receiving areas are recesses formed in said carrier tape.

18. A count and capture system comprising a base station and a removable cassette reversibly installable to the base station;
the removable cassette comprising:
a cassette housing,
a first reel adapted to supply a carrier tape along a first pathway through the cassette housing,
a second reel adapted to supply a cover tape along a second pathway through the cassette housing,
a third reel adapted to receive and accumulate a capture tape that comprises portions of said carrier tape and said cover tape that have been adhered together upstream along said first pathway within said cassette housing,
a deposit station located along said first pathway and comprising a deposit window in the cassette housing adapted to accommodate insertion therethrough a plurality of surgical-implements to be deposited successively onto said carrier tape at longitudinally spaced-apart receiving areas thereof when resident respectively in said deposit station, and
a counting station located along said first pathway downstream of said deposit station, the counting station comprising a counting window in the cassette housing; and
the base station comprising:
a sensor adapted to penetrate said counting window when the cassette housing is installed to the base station such that said sensor is disposed adjacent to said first pathway in the counting station, said sensor being adapted to detect said plurality of surgical-implements deposited on said carrier tape at the respective spaced-apart receiving areas thereof when resident in said counting station.

19. The count and capture system of claim 18, the base station comprising at least one drive sprocket adapted to engage with and drive one or more of said first, second and third reels in order to advance the carrier tape and the cover tape within the removable cassette.

20. The count and capture system of claim 18, said plurality of receiving areas being recesses formed in said carrier tape.

21. A method of counting and capturing surgical-implements comprising:
indexing a carrier tape comprising a plurality of predefined, spaced-apart receiving areas along a first pathway;
depositing respective surgical-implements into successive ones of said receiving areas as each said receiving area is located at a deposit station located along the first pathway;
after depositing each of the respective surgical-implements, indexing a cover tape along a second pathway that intersects the first pathway at a location downstream of the deposit station so that the cover tape is applied to the carrier tape to capture each of the respective surgical implements in the successive receiving areas,
detecting the respective surgical-implements in the successive receiving areas by a sensor at a counting station; and
recognizing or classifying the respective surgical-implements based on detecting them,
wherein a removable cassette comprises the carrier tape and the cover tape following the respective first and second pathways, the removable cassette being removably installable to a base station comprising the sensor.

22. The method of claim 21, further comprising:
after recognizing or classifying each of the respective surgical-implements, accumulating the respective surgical-implements in a capture tape comprising portions of the carrier tape and the cover tape that have been laminated together at a location downstream of the counting station.

23. The method of claim 21, wherein the respective surgical-implements are needles, the method further comprising:
before depositing each of the needles, trimming suture threads from each of the needles via a suture trimming system.

* * * * *